US00PP31883P2

(12) United States Plant Patent
Snijder

(10) Patent No.: US PP31,883 P2
(45) Date of Patent: Jun. 16, 2020

(54) ***PELARGONIUM* PLANT NAMED 'PEQZ0063'**

(50) Latin Name: *Pelargonium interspecific*
Varietal Denomination: PEQZ0063

(71) Applicant: SYNGENTA PARTICIPATIONS AG, Basel (CH)

(72) Inventor: Ronald Christiaan Snijder, Andijk (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 16/350,814

(22) Filed: Jan. 15, 2019

(51) Int. Cl.
*A01H 5/02* (2018.01)
*A01H 6/42* (2018.01)

(52) U.S. Cl.
USPC ..... Plt./324
CPC ..... *A01H 6/425* (2018.05)

(58) Field of Classification Search
USPC ..... Plt./324, 329
CPC ..... A01H 6/425; A01H 5/02
See application file for complete search history.

*Primary Examiner* — Keith O. Robinson
(74) *Attorney, Agent, or Firm* — Dale Skalla

(57) ABSTRACT

A new *Pelargonium* plant named 'PEQZ0063' particularly distinguished by the lavender colored semi-double inflorescences held above dark green foliage, heat and drought tolerant and edema tolerance on a spreading well-branched plant habit.

1 Drawing Sheet

Latin name of the genus and species of the plant claimed: *Pelargonium interspecific.*

Varietal denomination: 'PEQZ0063'.

BACKGROUND OF THE NEW PLANT

The present invention comprises a new *Pelargonium*, botanically known as *Pelargonium interspecific*, and hereinafter referred to by the variety name 'PEQZ0063'.

'PEQZ0063' is a product of a planned-breeding program. The new cultivar 'PEQZ0063' has lavender colored semi-double inflorescences held above dark green foliage, heat and drought tolerant and edema tolerance on a spreading well-branched plant habit.

'PEQZ0063' originates from a hybridization in a controlled breeding program made in February 2011 in a greenhouse in Amatitlán, Guatemala. The female parent was an unpatented, proprietary plant of *P. peltatum* parentage, identified as 'PEL-084073-08' with white color florets and lighter green foliage when compared to 'PEQZ0063'.

The male parent of 'PEQZ0063' was an unpatented, proprietary plant of *P. interspecific* parentage, identified as 'k09-5007-1' with dark red colored florets and a more upright habit when compared to 'PEQZ0063'. The resultant seed was sown in December 2011.

'PEQZ0063' was selected as one flowering plant within the progeny of the stated cross in April 2012 in a greenhouse in Enkhuizen, The Netherlands.

The first act of asexual reproduction of 'PEQZ0063' was accomplished when vegetative stem cuttings were propagated from the initial selection in the May 2012 in a greenhouse in Enkhuizen, The Netherlands.

BRIEF SUMMARY OF INVENTION

Horticultural examination of plants grown from cuttings of the plant initiated in June 2012 in Enkhuizen, The Netherlands, and continuing thereafter, has demonstrated that the combination of characteristics as herein disclosed for 'PEQZ0063' are firmly fixed and are retained through successive generations of asexual reproduction.

'PEQZ0063' has not been observed under all possible environmental conditions. The phenotype may vary significantly with variations in environment such as temperature, light intensity, and day length.

A Plant Breeder's Right for this cultivar has not yet been applied for. 'PEQZ0063' has not been made publicly available prior to the effective filing date of this application, notwithstanding any disclosure that may have been made less than one year prior to the effective filing date of this application by the inventor or another who obtained 'PEQZ0063' directly from the inventor.

The following traits have been repeatedly observed and are determined to be the basic characteristics of the new variety. The combination of these characteristics distinguishes this *Pelargonium* as a new and distinct variety.

BRIEF DESCRIPTION OF THE PHOTOGRAPHS

Figure 1:
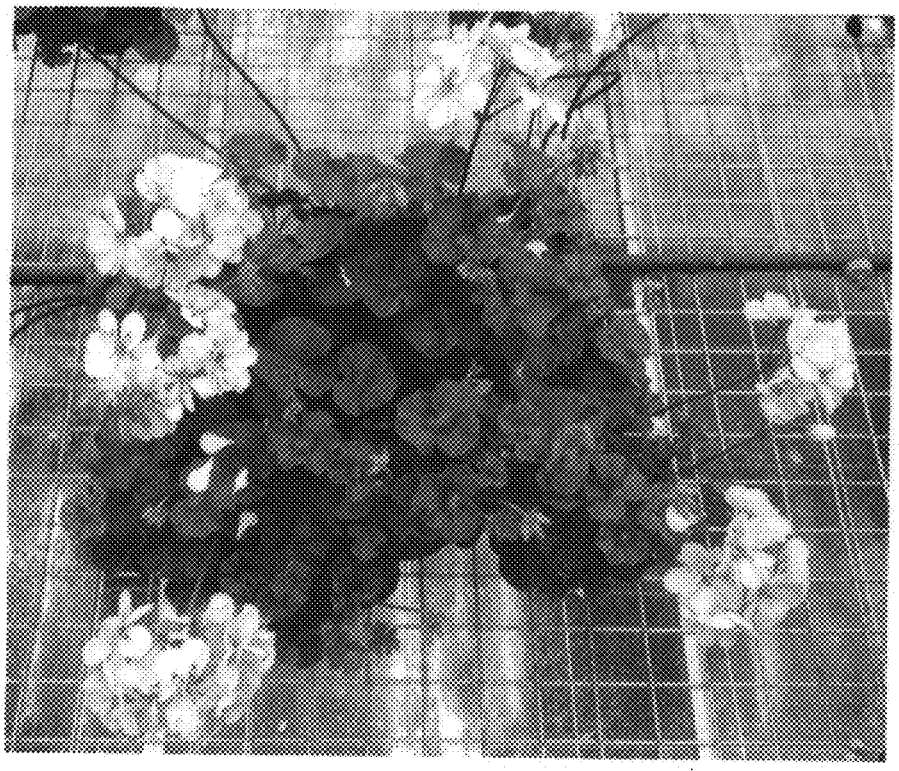
Figure 2:
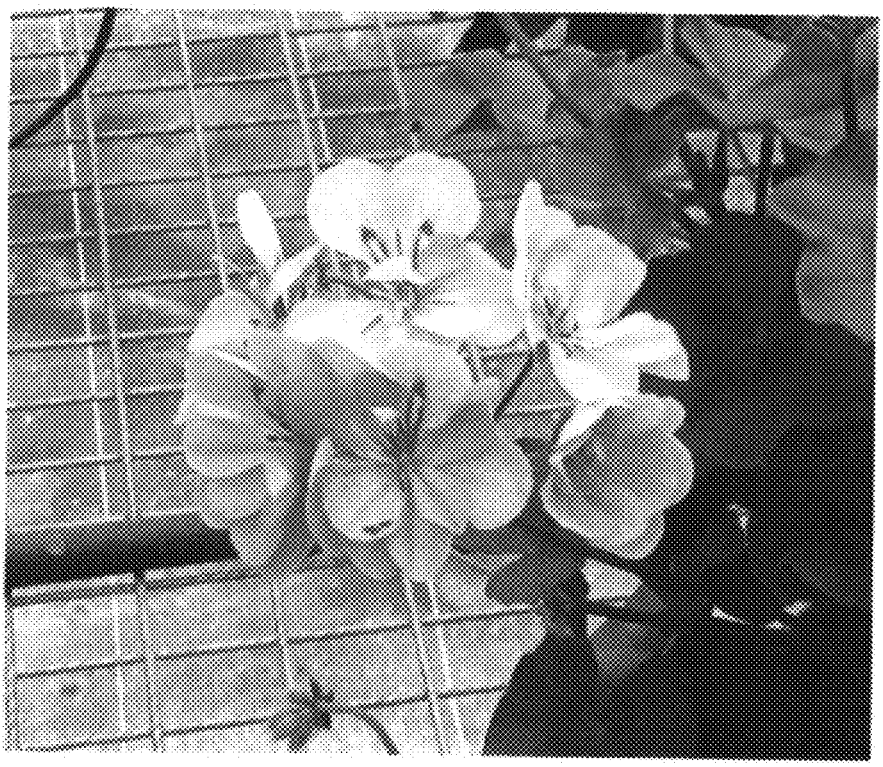

The accompanying photographic drawings show typical flower and foliage characteristics of 'PEQZ0063' with colors being as true as possible with an illustration of this type. The photographic drawings in FIG. 1, shows a basket with 4 flowering plants of the new variety and in FIG. 2, a close-up of the umbel.

DETAILED BOTANICAL DESCRIPTION

The plant descriptions and measurements were taken in Andijk, The Netherlands in September under natural light. These plants were approximately 12 weeks old and were grown in a 1 gallon pots, in a greenhouse trial. The plants shown in the photographs were about 25 weeks old growing in a 10 inch pot in a greenhouse. The photographs were taken in October 2018.

Color references are made to The Royal Horticultural Society Colour Chart (R.H.S.) 2001.

TABLE 1

DIFFERENCES BETWEEN THE NEW VARIETY 'PEQZ0063' AND A MOST SIMILAR VARIETY

| | 'PEQZ0063' | 'Fisam' (U.S. Plant Pat. No. 8,327) |
|---|---|---|
| Foliage color: | Dark green | Green |
| Floret petal color: | Light lavender | Dark lavender purple |

Plant:

*Form, growth and habit.*—Upright to semi-trailing.
*Plant height.*—18-20 cm.
*Plant height (inflorescence included).*—20-24 cm.
*Plant width.*—40-45 cm.

Roots:

*Number of days to initiate roots.*—15-18 days at about 22 degrees C.
*Number of days to produce a rooted cutting.*—21-23 days at 22 degrees C.
*Type.*—Fine, fibrous, free branching.
*Color.*—RHS N155B.

Foliage:

*Immature leaf, color upper surface.*—Closest to RHS 137A.
*Immature leaf, lower surface.*—Between RHS 137C and RHS 146A.
*Mature leaf, color upper surface.*—The very visible and dark veining gives the leaf a dark overall appearance, closest to RHS 137A. However, the actual color of the leaves in between the veining is of a much lighter green, closest to RHS 144A.
*Mature leaf, lower surface.*—Between RHS 137C and RHS 146A.
*Length.*—4.0-4.5 cm.
*Width.*—6.0-9.0 cm.
*Shape.*—Orbicular with irregular indents and wavy lobs.
*Base shape.*—Cordate, heart-shaped.
*Apex shape.*—Rounded, waved.
*Margin.*—Wavy, undulate margins.
*Texture upper side.*—Pilose.
*Texture lower side.*—Pilose.
*Leaf zonation color.*—RHS 202A.
*Variegation of the leaf blade.*—Absent.
*Color of veins, upper surface.*—Closest to RHS 133A and RHS 136A.
*Color of veins, lower surface.*—Closest to RHS 137A and RHS 137B.
*Pattern of veining.*—Palmate.
*Petiole color.*—Closest to RHS 144A mottled with anthocyanins of color RHS 187A.
*Petiole length.*—Range: 3.0-8.0 cm.
*Diameter of petiole.*—0.2-0.3 cm.
*Texture.*—Pilose hairs.

Stem:

*Quantity of branches.*—8-10.
*Color of stem.*—Closest to RHS 187A and RHS 187B (parts of stem/branches with strong anthocyanins), closest to RHS 144A and RHS 144B (green/younger parts).
*Length of stem.*—25-35 cm.
*Diameter.*—0.5-0.6 cm.
*Length of internodes.*—Range: 2.0-5.0 cm.
*Texture.*—Hirsute, pilose hairs.

Peduncle:

*Color of peduncle.*—Closest to RHS 144A and RHS 144B.
*Length of peduncle.*—8.0-15.0 cm (most peduncles between 8.0-11.0 cm).
*Peduncle diameter.*—0.3 cm.
*Texture.*—Hirsute.

Pedicel:

*Color of pedicel.*—Closest to RHS 187A and RHS 187B.
*Length of pedicel.*—2.0-2.2 cm.
*Diameter of pedicel.*—0.15-0.2 cm.
*Texture.*—Pilose.

Bud (just before opening):

*Color.*—Closest to RHS 65D.
*Length.*—About 2.5 cm.
*Width.*—0.9-1.1 cm.
*Shape.*—Elliptical.

Inflorescence:

*Type.*—Umbel, semi-spherical.
*Lastingness of individual flowers.*—7-9 days at 18° C. temperature.
*Number of inflorescences per plant.*—9 mature and 20 immature umbels in various stages.
*Width of the inflorescence.*—6-7 cm.
*Fragrance.*—None.
*Umbel diameter.*—*About* 8.0-10.0 cm.
*Umbel depth.*—*About* 5.0-5.5 cm.

Corolla:

*Form.*—Semi-double.
*Number of petals.*—8-10.
*Diameter of flower.*—4.0-5.0 cm.
*Depth of flower.*—2-2.5 cm.
*Color upper petals, upper surface.*—Closest to RHS 74D and RHS 78D, with strong red-purple (between RHS 46B and RHS 57A) marking (stripes and dots).
*Color upper petals, lower surface.*—Closest to RHS 74D but much whiter.
*Length of upper petals.*—About 3 cm.
*Width of upper petals.*—About 2 cm.
*Color lower petals, upper surface.*—Closest to RHS 74D and RHS 78D but much whiter, with strong marking (stripes and dots) of color closest to RHS 74A.
*Color lower petals, lower surface.*—Closest to RHS 66B.
*Length of lower petals.*—About 2.5 cm.
*Width of lower petals.*—About 1.5 cm.
*Petal shape.*—Obovate to spatulate.
*Apex shape.*—Rounded.
*Margin.*—Entire.
*Base.*—Attenuate.
*Petal texture, upper and lower surface.*—Pilose.

Calyx:

*Number of sepals.*—5.
*Color of sepals.*—Closest to RHS 144A and 144B, covered with anthocyanins closest to RHS 187A.
*Length of sepals.*—About 1.5 cm.
*Width of sepals.*—0.3-0.4 cm.
*Sepal shape.*—Lanceolate.
*Apex shape.*—Acute, with a sharp tip.
*Margins.*—Entire.
*Texture, upper surface.*—Pilose.

*Lower surface*.—Pilose.

Reproductive organs:

Gynoecium:

*Pistil*.—1.

*Length*.—1.0-1.1 cm.

*Style color*.—Closest to RHS 145D (base) and RHS 58A (apex).

*Style length*.—0.5-0.6 cm.

*Stigma color*.—Closest to RHS 60A.

*Ovary color*.—Closest to RHS 145A.

*Ovary length*.—0.4-0.5 cm.

*Ovary diameter*.—About 0.3 cm.

Androecium:

*Number of stamens*.—5.

*Color of filaments*.—Apex closest to RHS 66A, base closest to RHS 155C.

*Length filaments*.—1.0-1.2 cm.

*Anther color*.—Closest to RHS 70A, margins closest to RHS 81A.

*Length of anthers*.—About 0.3 cm.

*Color of pollen*.—Closest to RHS 28A.

*Pollen amount*.—Scarce.

*Fertility/seed set*.—Has not been determined to date.

*Disease/pest resistance*.—Edema tolerance.

What is claimed is:

1. A new and distinct variety of *Pelargonium* plant named 'PEQZ0063' substantially as illustrated and described herein.

* * * * *